United States Patent [19]

Miyaura et al.

[11] Patent Number: 6,150,115
[45] Date of Patent: Nov. 21, 2000

[54] QUANTITATIVE DETERMINATION METHOD FOR HEPARAN SULFATE AND DIAGNOSTIC METHOD USING THE SAME

[75] Inventors: Shuichi Miyaura, Kanagawa; Sawako Takeshita; Takeshi Ishimaru, both of Tokyo, all of Japan

[73] Assignee: Seikagaku Kogyo Kabushiki Kaisha, Tokyo, Japan

[21] Appl. No.: 09/055,106

[22] Filed: Apr. 3, 1998

[30] Foreign Application Priority Data

Apr. 4, 1997 [JP] Japan ................................. 9-102685

[51] Int. Cl.$^7$ ..................... G01N 33/53; G01W 33/535; A61K 39/00; A61K 39/38
[52] U.S. Cl. ........................ 435/7.1; 435/7.1; 435/7.9; 435/7.92; 435/7.93; 424/184.1; 514/866; 514/56
[58] Field of Search ........................ 435/7.1, 7.9, 7.92, 435/7.93; 424/184.1; 514/866, 56

[56] References Cited

FOREIGN PATENT DOCUMENTS

| 0 313 538 A22 | 4/1989 | European Pat. Off. . |
|---|---|---|
| 63-052889 | 3/1988 | Japan . |
| 63-112994 | 5/1988 | Japan . |
| 02156898 | 6/1990 | Japan . |
| WO 90/06954 | 6/1990 | WIPO . |
| WO 90/08957 | 8/1990 | WIPO . |
| WO 97/40174 | 10/1997 | WIPO . |

OTHER PUBLICATIONS

Yokoyama et al, The 11th Diabetic Nephropathy Meeting held in Nagoya, Japan on Oct. 4–5, 1997.

Satoh et al, The 9th Japan Diabetic Nephropathy Seminar Abstracts in Tokyo, Japan on Nov. 15–16, 1997.

Product Report No. 90, Sep. 1, 1995, Seikagacu Corporation (with English subtitles).

Jacob van Den Born, et al., A Monoclonal antibody agaist GBM heparan sulfate induces an acute selective proteinuria in rats, International Society of Nephrology, Kidney international, vol. 41(1992), pp. 115–123.

J.T. Tamsma, et al., Expression of glomerular extracellular matrix components in human diabetic nephropathy: decrease of heparan sulphate in the glomerular basement membrane. Diabetologia (1994)37:313–320.

J. van den Born, et al., Selective proteinuria in diabetic nephropathy in the rat is associated with a relative decrease in glomerular basement membrane heparan sulphate, Diabetologia (1995)38:161–172.

Nicole F. van Det, et al., Effects of high glucose on the production of heparan sulfate proteoglycan by mesangial and epithelial cells. International Society of Nephrology, Kidney International, vol. 49(1996), pp. 1079–1089.

Diabetes, The 40th Japan Diabetes Associate annual Learning Meeting Program & Abstracts, May 22–24, 1997 at Tokyo, Japan, Japan Diabetes Associate, Issued Apr. 21, 1997.

The 11th Diabetic Nephropathy Meeting held in Nagoya, Japan on Oct. 4–5, 1997.

The 9th Japan Diabetic Nephropathy Seminar Abstracts in Tokyo, Japan on Nov. 15–16, 1997.

The 12th Japan Diabetic Animal Seminar Program Lecture Abstract in Osaka, Japan on Feb. 6–7, 1998.

The 41th Japan Diabetes Associate Annual Learning Meeting Pamphlet in Wakayama, Japan on May 20–21, 1998.

Product Report No. 10 Monoclonal Anti Heparan Sulfate, 10E4, Monoclonal Anti Heparan sulfate, 3G10 by Seikagaku Corporation.

J. Van Den Born, et al., Production and Characterization of a Monoclonal antibody Against Human Glomerular Heparan Sulfate, Laboratory Investigation, vol. 65, No. 3, pp. 287–297, 1991.

*Primary Examiner*—Nita Minnifield
*Assistant Examiner*—Padma Baskar
*Attorney, Agent, or Firm*—Knobbe, Martens, Olson & Bear, LLP

[57] ABSTRACT

The present invention relates to a quantitative determination method for heparan sulfate in body fluid specimens of various chronic diseases, in urine samples of diabetic nephropathy and for diagnosing hepatic diseases and rheumatoid arthritis in blood specimens. And also this method provides a diagnostic tool for judging the condition of diabetic nephropathy, hepatic diseases and rheumatoid arthritis by determination of changes by use of aforementioned quantitative determination of heparan sulfate.

20 Claims, 7 Drawing Sheets

QUANTITATIVE DETERMINATION METHOD FOR HEPARAN SULFATE AND DIAGNOSTIC METHOD USING THE SAME

BACKGROUND OF THE INVENTION

1. Field of the Invention

The present invention relates to a quantitative determination method for heparan sulfate contained in body fluid specimens, which method is useful for identifying various diseases. The present invention also provides means for judging the condition of diabetic nephropathy by determination of heparan sulfate contained in urine specimens by use of the quantitative determination method of the present invention. The present invention further provides means for diagnosing hepatic diseases and rheumatoid arthritis by determination of heparan sulfate contained in blood specimens by use of the quantitative determination method of the present invention.

2. Description of the Related Art

Diabetes is known to cause various complications. Among the fatal complications caused by diabetes is "diabetic nephropathy," which results in grave renal failure.

In healthy kidneys, a negative charge in the heparan sulfate sugar chain of heparan sulfate proteoglycan that is present in the glomerular basement membrane functions as a "charge barrier" against protein and the like in blood and prevents protein and the like from being deposited on the glomeruli or leaking into urine (*Proc. Natl. Acad. Sci. USA* 76:1303, 1979).

However, it often happens that the glomerular basement membrane of a patient suffering from diabetic nephropathy is damaged and the function as a "charge barrier" is lost. For diagnosis of diabetic nephropathy, there has conventionally been employed a method in which albumin that has leaked into urine after passing through the "charge barrier" is measured and the quantity is compared with a normal value of a healthy person, to thereby determine incipiental diabetic nephropathy.

As a method for measuring heparan sulfate, a method of using anti-heparan sulfate antibody JM403 has been known. However, the anti-heparan sulfate antibody is known to exhibit cross-reactivity to hyaluronic acid (*Kidney International*, 41(1992) pp115–123). Therefore, the method, being unable to provide accurate measurement of heparan sulfate, is impractical as a method for measuring only heparan sulfate, and cannot be used in the diagnosis of diseases.

Patients suffering from diabetes run a high risk of developing diabetic nephropathy. Diabetes and diabetic nephropathy are classified as follows depending on urine albumin: 1) diabetes (high blood sugar level/creatinine-corrected (CR) urine albumin: less than 12 mg/gCR; also described as DM1 hereinafter), 2) incipiental diabetic nephropathy (high blood sugar level/creatinine-corrected (CR) urine albumin: 12 mg/gCR or higher and less than 200 mg/gCR; also described as DM2 hereinafter), and 3) diabetic nephropathy (high blood sugar level/creatinine-corrected (CR) urine albumin: 200 mg/gCR or higher; also described as DM3 hereinafter).

Renal pathosis is not detected in patients in the stage of DM1. Patients in the stage of DM2 have minor renal pathosis, and their condition may be improved to DM1 by proper treatment. However, patients in the stage of DM3 have grave renal pathosis, which may hardly be improved even by proper treatment.

Thus, because prognosis after a true onset of diabetic nephropathy is very unfavorable, the progression of diabetic nephropathy must be diagnosed as early as possible.

However, the level of albumin contained in an urine specimen, which has conventionally been used as a diagnostic index for diabetic nephropathy, varies even in a healthy person, and therefore it is difficult to accurately judge, solely by the albumin level, the condition of patients suffering from diabetes whose stage may be in progress from diabetes (DM1) to incipiental diabetic nephropathy (DM2), or further to diabetic nephropathy (DM3).

In addition, there are many cases in which proper treatment is commenced when, based on a change in the level of albumin contained in a urine specimen, a patient is given a definite diagnosis of incipiental diabetic nephropathy or diabetic nephropathy, yet the treatment turns out to be ineffective, leading to grave nephropathy or further to renal failure.

Accordingly, a first subject of the present invention is the provision of means for specifying as early as possible patients suffering from diabetes who according to the classification based on the level of albumin in a urine specimen do not yet have incipiental diabetic nephropathy, but are in the course of the progression to incipiental diabetic nephropathy, or patients suffering from incipiental diabetic nephropathy who are in the course of the progression to diabetic nephropathy.

In many hepatic diseases, pathological changes occur very slowly in their early stage. Thus, it often happens that by the time pathosis is detected, the condition has progressed too far for the patient to be saved or the patient must undergo treatment for many years.

Conventional methods for detecting hepatic diseases include assays of hepatopathy markers such as blood cholinesterase, hepaplastin, GOT, GPT, γGTP, bilirubin, and immunoglobulin; as well as a liver function test. Also, measurement of urine bilirubin is used to screen for hepatic diseases. In addition, image diagnosis by CT scanning is used to detect hepatic diseases. Moreover, for diagnosis of the causes of hepatic diseases, anti-hepatitis virus antibody/antigen is tested.

There is also provided a method for diagnosis of hepatic diseases by the detection of fibrogenesis caused by hepatic diseases. For example, a histologic detection method in which a biopsy of the liver is performed by laparoscopy or the like is provided.

However, these diagnostic methods have drawbacks such as sampling errors and invasion of the living body. A proposed method to detect fibrogenesis in the liver caused by hepatic diseases based on the rise in blood γ-globulin or the like has also been found unsatisfactory. Accordingly, none of these methods are effective for detecting hepatic diseases.

The criteria set by the American Rheumatology Society are currently used to diagnose rheumatoid arthritis. A blood test, which is an objective test among the criteria, includes only one measurement item, i.e. rheumatoid factor. However, a test for rheumatoid factor is known to be not highly specific. A test for anti-rheumatoid factor antibody (IgG-RF) is also performed, but used only in patients who have already been diagnosed as having rheumatism, so as to judge the seriousness of their arthritis and whether they have angitis or not.

Thus, an effective method for diagnosis of rheumatoid arthritis has not yet been developed, and the diagnosis is made based on subjective symptoms reported by patients.

Although the level of hyaluronic acid in blood is known to rise in patients suffering from rheumatoid arthritis, detecting rheumatoid arthritis based on this finding is difficult and does not provide an accurate method for detection. Another known method of judging the condition of rheumatoid arthritis uses an index based on the degree of the patient's mobility in daily life and ability to exercise such as degrees of dysfunction (class classification by Steinbrocker et al.), activity index (Ransbury index), conditions of joints (stage classification). The method permits judgment of conditions, but does not provide an accurate judgment because the judgment is not quantitative and is based on subjective symptoms reported by patients, which may vary a great deal among patients.

As described above, various means for detecting hepatic diseases and rheumatoid arthritis have been provided, but none of the methods are satisfactory.

As a result, accurate diagnosis of hepatic diseases and rheumatoid arthritis requires a large number of tests, which is complicated and unsuitable for screening a large number of specimens.

Accordingly, a second subject of the present invention is the provision of means for diagnosing hepatic diseases and rheumatoid arthritis accurately and which permits simple primary screening of a large number of specimens.

SUMMARY OF THE INVENTION

The inventors of the present invention have conducted careful studies in an attempt to attain the above-mentioned first subject, based on the finding that dysbolism of heparan sulfate in the basement membrane occurs prior to a structural change in the glomerulus of patients suffering from diabetic nephropathy. As a result of the studies, the inventors of the present invention have found that heparan sulfate changes quantitatively and/or qualitatively contained in urine of patients suffering from diabetic nephropathy and having impairment in the glomerulus in the course of the development to the nephropathy, and that the above-mentioned first object is attained by specifying the changes.

In an attempt to attain the second subject of the present invention, the inventors have also carried out careful studies regarding pathological changes in hepatic diseases and rheumatoid arthritis by use of various specimens, and found that heparan sulfate contained in blood of patients suffering from hepatic diseases or rheumatoid arthritis changes quantitatively and/or qualitatively, and that on the basis of these changes hepatic diseases and rheumatoid arthritis can be detected with a high degree of sensitivity.

Based on these findings, the inventors of the present invention provide a simple and accurate quantitative determination method for heparan sulfate contained in body fluid specimens, which provides the basis for diagnosing diseases. In other words, the quantitative determination method of the present invention is very easy to perform and allows even unskilled persons to screen a large number of specimens at one time because the antigen-antibody reaction between heparan sulfate and an anti-heparan sulfate antibody is used. In addition, because the value of quantitative determination can be expressed numerically even when a large number of specimens are determined, heparan sulfate is quantitatively determined with accuracy by use of the quantitative determination method for heparan sulfate of the present invention.

The inventors of the present invention also provide a diagnostic method for the progressing stage to diabetic nephropathy, by specifically determining quantitative and/or qualitative changes of heparan sulfate, particularly the changes of glucosamine residues with an N-sulfate group in heparan sulfate, contained in urine specimens of the diabetic; as well as a kit for performing the diagnostic method.

Further, the inventors of the present invention provide a method for detecting hepatic diseases or rheumatoid arthritis by detecting quantitative and/or qualitative changes of heparan sulfate, particularly the changes of glucosamine residues with an N-sulfate group in the heparan sulfate, in blood; as well as a kit for performing the detection method.

DETAILED DESCRIPTION OF THE PREFERRED EMBODIMENTS

Figure 1:
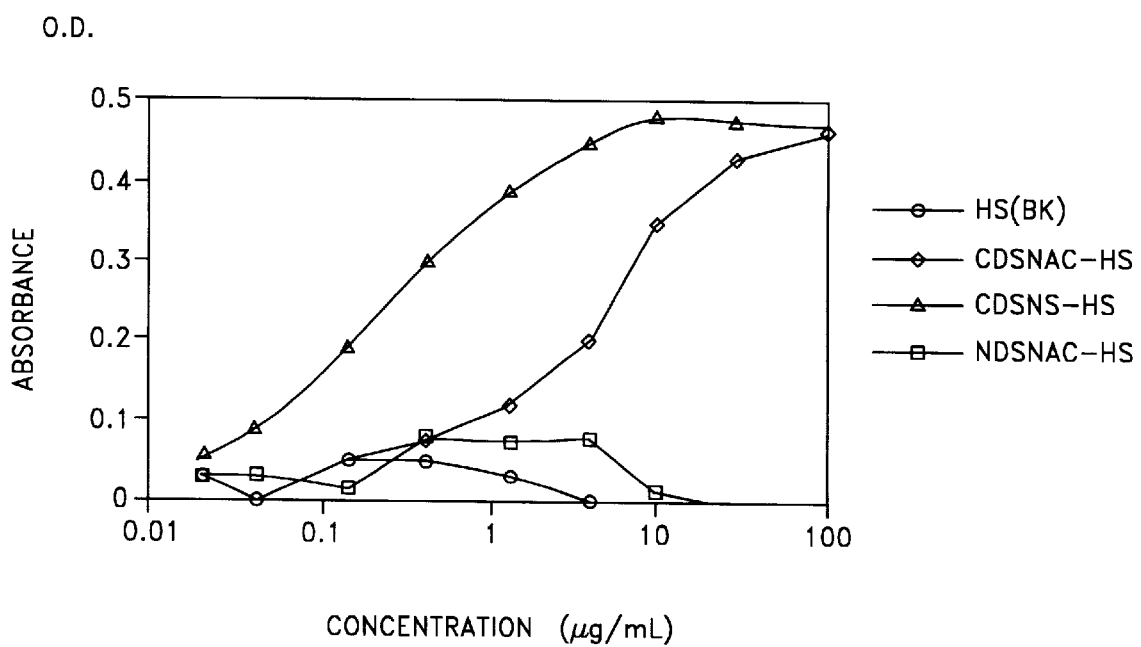
FIG. 1 shows the changes in the recognition ratio of anti-heparan sulfate antibody 10E4 corresponding to the changes in the sulfate group content in heparan sulfate.

The present invention will next be described in detail.

A. Quantitative Determination according to the Present Invention

Heparan sulfate, the object substance to be quantitatively determined in the present invention, is sulfated polysaccharide found in the cell membrane and basement membrane of a mammal in the form of proteoglycan (may be referred to as "heparan sulfate proteoglycan" in the present specification) which is bound to a protein in the lungs, liver, kidneys, brain, spleen, aorta, etc. The basic sugar chain structure of heparan sulfate is made up of repeating units comprising a D-glucosamine and a hexuronic acid (D-glucuronic acid and L-iduronic acid) wherein the N-position and the 6- position of the D-glucosamine are sulfated and the 2- position of the hexuronic acid is sulfated, in common with heparin. As compared to heparin, heparan sulfate has a low content of a sulfate group, L-iduronic acid, and N-sulfated glucosamine, and exhibits very low blood anti-coagulation activity.

In the present invention, "quantitative determination" is used to refer to determination of changes in the quantity of heparan sulfate detected by a method which, if at all, permits detection of heparan sulfate; e.g., determination of change in the quantity of a specific heparan sulfate in which a certain residue thereof has undergone modification; the molecular weight; the quantity of the sulfate residue, or the quantity of heparan sulfate having a sulfate group at a specific site.

The method for diagnosing the progressing stage to diabetic nephropathy and the method for diagnosing hepatic diseases or rheumatoid arithritis according to the present invention essentially call for a simple and accurate determination method for heparan sulfate contained in a body fluid specimen such as a urine specimen or a blood specimen.

In order to practice these diagnosis methods according to the present invention, it is therefore technically essential to establish a determination method which can accurately determine heparan sulfate contained in a body fluid specimen.

The present invention also provides a quantitative determination method for heparan sulfate contained in a body fluid specimen.

Examples of the quantitative determination method for heparan sulfate of the common form contained in a body fluid specimen include the disaccharide analysis method employing decomposition by a heparitinase and high-performance liquid chromatography (HPLC) in combination, an analysis employing HPLC and gel filtration, and a method based on the principle of antigen-antibody reaction between heparan sulfate and an anti-heparan sulfate antibody. Although no particular limitation is imposed on the determination method so long as the determination of heparan sulfate contained in a specimen is technically possible, the method based on the principle of antigen-antibody reaction between heparan sulfate and an anti-heparan sulfate antibody is preferred.

Examples of the preferable method employing the principle of antigen-antibody reaction include (1) a method employing antigen-antibody reaction of an anti-heparan sulfate antibody attached to a solid phase (described below) with labeled heparan sulfate and heparan sulfate contained in a specimen; (2) a method employing antigen-antibody reaction of anti-heparan sulfate antibody with heparan sulfate contained in a specimen and heparan sulfate attached to a solid phase; and (3) a method of determination of heparan sulfate contained in a body fluid specimen wherein the body fluid specimen and an anti-heparan sulfate antibody are successively brought into contact with a heparan sulfate-fixed microgranular solid phase (described below) to aggregate the microgranular solid phase.

No particular limitation is imposed on the elements (e.g., a solid phase (including a microgranular solid phase), labeled heparan sulfate, and an antibody such as an anti-heparan sulfate antibody) used in the determination method employing these antigen-antibody reactions, and they may be selected according to the embodiment of a specific determination method. Typical embodiments of each element will be described.

Examples of the solid phase on which an anti-heparan sulfate antibody or heparan sulfate is fixed include a microplate, a bead, a tube, a membrane, a gel, and a microgranular solid phase (e.g., gelatin particles, kaolin particles, and synthetic polymer particles (such as latex particles)). Of these, a microplate, a bead, a tube, or a microgranular solid phase is preferably used. A microplate is particularly preferable, in view of particularly accurate determination characteristics and simplicity at the determination.

Examples of the determination method employing antigen-antibody reaction using an anti-heparan sulfate antibody-fixed microplate include 1) a method employing competitive antigen-antibody reaction between heparan sulfate contained in a body fluid specimen and labeled heparan sulfate combined with a labeling substance with respect to an anti-heparan sulfate antibody induced through simultaneous addition of the body fluid specimen and said labeled heparan sulfate to the anti-heparan sulfate antibody-fixed microplate and 2) a method of determination of heparan sulfate contained in a body fluid specimen employing inhibitory antigen-antibody reaction wherein the body fluid specimen is brought into contact with an anti-heparan sulfate antibody-fixed microplate to bind heparan sulfate contained in the body fluid specimen to the anti-heparan sulfate antibody on the microplate, and subsequently labeled heparan sulfate is brought into contact with the microplate to bind it exclusively to the anti-heparan sulfate antibody on the microplate with inhibiting heparan sulfate derived from the body fluid specimen bound to the anti-heparan sulfate antibody on the microplate.

The above-described determination method employing fixation of the anti-heparan sulfate antibody on the microplate is a particularly preferable embodiment of the determination, in view of facilitating simultaneous determination of a large number of body fluid specimens.

The anti-heparan sulfate antibody can be attached to an solid phase such as a microplate according to a typically employed method such as a physical adsorption method, a covalent bond method, or an inclusion method. No particular limitation is imposed on the fixation method of the anti-heparan sulfate antibody on the solid phase, and the physical adsorption method is preferred in view of operational simplicity.

Furthermore, typical determination embodiments include a method employing a heparan sulfate-fixed microplate.

For example, there is provided a method of determination of heparan sulfate contained in a body fluid specimen employing competitive or inhibitory antigen-antibody reaction, wherein a body fluid specimen is added to a heparan sulfate-fixed microplate to react heparan sulfate attached to the microplate and heparan sulfate contained in the body fluid specimen with an anti-heparan sulfate antibody and subsequently the anti-heparan sulfate antibody bound to heparan sulfate attached to the microplate is detected through a labeled secondary antibody, etc.

The labeled heparan sulfate to be used in the series of the determination methods combines with a labeling substance. Examples of the labeling substance include a counterpart of specific binding pairs (e.g., biotin and avidin such as streptavidin; or lectin and sugar chain); a fluorescent substance such as FITC, phycoerythrin, europium, phycocyanin, Rhodamin, Texas Red, umbelliferone, Tricolor, cyanin, or 7-amino-4-methylcoumarine-3-acetic acid (AMCA); an enzyme such as alkaliphosphatase, $\beta$-galactosidase, peroxidase, or glucose-oxidase; a hapten such as dinitrofluorobenzene, AMP (adenosine monophosphate), or 2,4-dinitroaniline; and a radioactive isotope such as $^{125}I$, $^{131}I$, or $^{3}H$. No particular limitation is imposed on the labeling substances, and a counterpart of the above-described specific binding pairs is preferred, with a counterpart of avidin-biotin system of specific bonding pair being particularly preferred.

These labeling substance may be combined with heparan sulfate through a customary method.

For example, heparan sulfate is labeled through reaction with biotin hydrazide in the presence of added EDC (1-ethyl-3(3-dimethylaminopropyl)carbodiimide) dissolved in MES [(2-N-morpholino)ethanesulfonic acid], etc. In the labeling method, unreacted biotin hydrazide may be removed through a usual method such as dialysis, fractionation with ethanol, or ultrafiltration. The dialysis is advantageous for easily obtaining biotin-labeled heparan sulfate.

Moreover, each labeling substance can be determined through a determination method which has already been established for each labeling substance.

For example, biotin-labeled heparan sulfate is indirectly determined by binding it with streptavidin (labeled; preferably labeled with a specific enzyme such as peroxidase which is easily determined) having high affinity to biotin.

When the above-described peroxidase is used for labeling streptavidin, there are preferably used a substrate coloring by peroxidase typically used for this purpose such as tetramethylbenzidine (TMB) and hydrogen peroxide.

No particular limitation is imposed on the labeled secondary antibody used to detect the above-described anti-heparan sulfate antibody, and it is suitably selected according to the origin and kind of the primary antibody (anti-heparan sulfate antibody); i.e., when the primary antibody is derived from a rabbit, it is an antibody to rabbit immunoglobulin, whereas when the primary antibody is derived from a mouse, it is an antibody to mouse immunoglobulin. Examples of a substance labeling a secondary antibody include substances described as those labeling the above-described heparan sulfate. Of these, enzymes are typically used. The substances labeling a secondary antibody and the detection method of the labeling substances may be selected according to needs. Examples of the combination of the anti-heparan sulfate antibody and the labeled secondary antibody include a combination of mouse-IgM antibody (e.g., anti-heparan sulfate monoclonal antibody 10E4) and peroxidase-labeled anti-mouse-IgM antibody.

As described above, embodiments other than those employing a microplate may be applied in the determination according to the present invention. Typical embodiments not employing such a microplate include a method employing aggregation reaction based on use of the above-described microgranular solid phase as an index.

For example, heparan sulfate contained in a body fluid specimen may be determined by the following steps: preparing a mixture solution of the body fluid specimen and a heparan sulfate-fixed microglanular solid phase comprising synthetic polymer particles such as latex particles; further adding an anti-heparan sulfate antibody into a mixture solution to induce aggregation reaction of the latex particles via antigen-antibody reaction; and detecting the inhibition degree of the aggregation reaction caused by heparan sulfate contained in the body fluid specimen.

The antibody used in the determination method employing the above-described series of antigen-antibody reaction may be a monoclonal antibody or a polyclonal antibody so long as it is an anti-heparan sulfate antibody recognizing heparan sulfate. However, an antibody having a specificity to heparan sulfate and no cross-reactivity to hyaluronic acid is preferred. Furthermore, a monoclonal antibody having a specificity to a specific antigenic determinant in heparan sulfate (the antibody recognizes a specific the antigenic determinant to induce antigen-antibody reaction) is preferably used in order to obtain a result with higher accuracy. Example of preferable anti-heparan sulfate antibody is anti-heparan sulfate monoclonal antibody sold under the trade name 10E4 or F58-10E4 manufactured by Seikagaku Kogyo Kabushiki Kaisba, Tokyo, Japan and anti-heparan sulfate monoclonal antibody sold under the trade name HepSS-1 manufactured by Seikagaku Kogyo Kabushiki Kaisha, Tokyo, Japan, and anti-heparan sulfate monoclonal antibody 10E4 is particularly preferable.

The monoclonal antibody to heparan sulfate may be manufactured through a known method; i.e., selecting a clone producing a desired antibody from hybridomas of myeloma cells and splenocytes.

Thus, there is provided the determination method according to the present invention.

B. Diagnosis Method According to the Present Invention a) Diagnosis of the Development of Diabetic Nephropathy As described above, in a healthy kidney, negative charges in the heparan sulfate sugar chains of heparan sulfate proteoglycan in the glomerular basement membrane work as a "charge barrier" to prevent deposition of proteins in blood, to the glomerulus and leakage of proteins into urine.

In the present invention, progressing stage from diabetes to diabetic nephropathy may be diagnosed through determination of the heparan sulfate contained in a urine specimen by the determination method according to the present invention.

Thus, the above-described progressing stage from diabetes (DM1) to incipiental diabetic nephropathy (DM2) and further progression to diabetic nephropathy (DM3) may be diagnosed by the present invention. In other words, diagnosis of "an early stage of progression to diabetic nephropathy," i.e., progressing stages between pathological classes of diabetic nephropathy, conventionally diagnosed by an albumin content in a urine specimen, may be performed by the present invention.

The quantity of normal-form heparan sulfate contained in a urine specimen tends to decrease significantly during development from diabetes to diabetic nephropathy. In the present invention, the condition of a desired diabetic may be characterized through use, as an index, of variation in the quantity of normal-form heparan sulfate contained in a urine specimen.

In the present invention, when the determined quantity of normal-form heparan sulfate contained in a urine specimen of diabetic is less than the normal value, progression from diabetes to diabetic nephropathy is suggested as diagnosis of the condition of the diabetic.

In the present invention, "a urine specimen" includes urine, glomerular filtrate, or a liquid component obtained from urine or glomerular filtrate by removal of hemocyte components, etc.

For example, when the detected quantity of heparan sulfate is less than a predetermined threshold value of heparan sulfate contained in a urine specimen, diagnosis of "a progressing stage from diabetes to diabetic nephropathy" can be made, whereas when the detected value is greater than the predetermined threshold value, the progressing stage is denied. Thus, the progressing stage from diabetes to diabetic nephropathy can be diagnosed, leading to the provision of the method of the present invention for diagnosing the condition of a diabetic.

The N-sulfate group content of the glucosamine residues of heparan sulfate found in the glomerular basement membrane particularly tends to decrease in company with the progression of diabetic nephropathy (*Diabetologia*, 38, 161–172 (1995)). Thus, an antibody, exhibiting specificity at least for the antigenic determinant of the glucosamine residue with an N-sulfate group in heparan sulfate is preferably used as the above-described anti-heparan sulfate antibody.

When a monoclonal antibody is used, a monoclonal antibody, exhibiting specificity for the antigenic determinant of the glucosamine residue with an N-sulfate group in heparan sulfate is particularly preferred.

Examples of the monoclonal antibody include anti-heparan sulfate antibody 10E4 and HepSS-1 (products of Seikagaku Corp.).

For example, when a monoclonal antibody, exhibiting specificity for the antigenic determinant of the glucosamine residue with an N-sulfate group in heparan sulfate, such as anti-heparan sulfate antibody 10E4, is used as an element of the determination, the threshold value is set at 3–40 EU/mg CR, preferably 5–30 EU/mg CR (definition of "EU" used herein will be described in the Examples section).

Furthermore, the determination method of the present invention may be used in itself in order to diagnose a condition of a diabetic, or used in combination with another index such as a conventional albumin value in a urine specimen to further enhance reliability.

b) Diagnosis of Hepatic Diseases or Rheumatoid Arthritis

As described above, the quantity and/or quality of heparan sulfate contained in blood of a patient suffering from hepatic disease or rheumatoid arthritis tend to be different from those of a healthy person.

The quantity of heparan sulfate contained in blood of a patient suffering from hepatic disease or rheumatoid arthritis, particularly heparan sulfate having the glucosamine residues with an N-sulfate group tends to significantly decrease as compared with that in a healthy person.

In the present invention, a hepatic disease or rheumatoid arthritis may be diagnosed through use, as an index, of variation in the quantity of heparan sulfate contained in a blood specimen as compared with that in a healthy person. In other words, when the quantity of the above-described heparan sulfate detected from the blood specimen is less than the range of heparan sulfate value of a healthy person, the subject is proven to suffer from hepatic disease or rheumatoid arthritis. Thus, a hepatic disease or rheumatoid arthritis may be diagnosed.

In the present invention, "a blood specimen" refers to a liquid derived from blood (whole blood, serum, plasma, etc.). Of these, serum or plasma is preferably employed in order to more accurately reflect pathologic conditions of a hepatic disease or rheumatoid arthritis.

Incidentally, a N-sulfate group content in the glucosamine residues is considered to be an important physiological active factor in the structure of the sugar chain of heparan sulfate, and it is clarified that the quantity of the glucosamine residues with an N-sulfate group in heparan sulfate contained in a blood specimen is considered to decrease in the case of a patient suffering from hepatic disease or rheumatoid arthritis. Therefore, confirming existence and the quantity of the glucosamine residues with an N-sulfate group in heparan sulfate contained in a blood specimen is preferred in the diagnosis of a hepatic disease or rheumatoid arthritis. From these viewpoints, the above-described anti-heparan sulfate antibody is preferably an anti-heparan sulfate, exhibiting specificity for the antigenic determinant of the glucosamine residues with an N-sulfate group in heparan sulfate as in the above-described case of diagnosing progression of diabetic nephropathy.

When a monoclonal antibody is used as the above-described anti-heparan sulfate antibody, a monoclonal antibody exhibiting specificity for the antigenic determinant of the glucosamine residues with an N-sulfate group in heparan sulfate, is particularly preferred. Examples of such monoclonal antibodies include anti-heparan sulfate antibody 10 E4 and anti-heparan sulfate antibody HepSS-1 (products of Seikagaku Corp.) as in the above-described case of diagnosing a progressing stage to diabetic nephropathy. These anti-heparan sulfate antibodies are preferred for the application of the present invention to a hepatic disease or rheumatoid arthritis in that each of them exhibits specificity for the antigenic determinant of the glucosamine residue with an N-sulfate group in heparan sulfate and exhibit no cross-reactivity to hyaluronic acid.

Thus, there is provided a diagnosis method for a hepatic disease or rheumatoid arthritis through determination of heparan sulfate contained in a specimen by use of an anti-heparan sulfate antibody.

For example, when the detected quantity of heparan sulfate is less than the threshold value which is pre-fixed through the determination method of the present invention as the quantity of heparan sulfate contained in a body fluid specimen between a healthy case and a patient suffering from hepatic disease or rheumatoid arthritis, there is diagnosed "suspected hepatic disease or rheumatoid arthritis" and the disease is further examined in detail through measurement of other parameters, whereas when the detected value is greater than the threshold value, there is diagnosed "very low possibility of hepatic disease or rheumatoid arthritis." Therefore, a hepatic disease or rheumatoid arthritis may be diagnosed and a diagnosis method thereof is provided.

The above-described threshold value varies depending on a certain factor such as a selected specimen, an antibody to be used, or the antigenic determinant, and should be determined suitably. For example, when there are used serum as a blood specimen; the glucosamine residues with an N-sulfate group in heparan sulfate of the above-described anti-heparan sulfate antibody such as 10E4 or HepSS-1 as the antigenic determinant; and a monoclonal antibody exhibits no cross-reactivity to hyaluronic acid as one of the determination means, the threshold value is determined to be preferably 20–250 EU/ml, in particular 30–150 EU/ml (definition of "EU/ml" described here is identical to the definition in the below-described "Examples" section).

The thus-practiced diagnosis method according to the present invention may be applied itself for screening of a plurality of specimens in the diagnosis of a hepatic disease or rheumatoid arthritis.

The present invention provides a more definite diagnosis method for a hepatic disease or rheumatoid arthritis through conventional examinations individually applied to cases in which a suspected hepatic disease or rheumatoid arthritis is proven from many subjects.

The diagnosis method according to the present invention is assumed to be practiced in combination with a test such as a liver disorder test, a liver function test, or a HBs antigen/antibody test in order to definitely diagnose a hepatic disease.

In order to definitely diagnose rheumatoid arthritis with more enhanced reliability, the diagnosis method according to the present invention may be practiced together with an index such as conventional diagnosis standard or an IgG-RF value in blood.

C. Kit According to the Present Invention

The kit for practicing determination method of the present invention enables determination of heparan sulfate contained in a body fluid specimen.

No particular limitation is imposed on the kit so long as it enables the determination simply, and the kit essentially contains an anti-heparan sulfate antibody and heparan sulfate as competitive substance (this heparan sulfate is described "competitive heparan sulfate" hereinafter). The kit is preferably constructed of an solid phase on which either an anti-heparan sulfate antibody or competitive heparan sulfate is fixed, i.e., an anti-heparan sulfate antibody-attached solid phase or competitive heparan sulfate-attached solid phase.

Moreover, the kit to practice the determination method according to the present invention most preferably contains (1) a reagent containing labeled heparan sulfate as the competitive heparan sulfate and (2) a reagent detecting a labeling substance of the labeled heparan sulfate.

Heparan sulfate such as the labeled heparan sulfate is preferably contained in a predetermined amount in the reagent in the kit and preferably exists at a homogeneous concentration in the system.

The labeling substance of the labeled heparan sulfate and the detecting substance thereto in the kit of the present embodiment may be selected according to the description of the above-described determination method according to the invention.

Also, the kit to practice the determination method according to the present invention may further contain as a component in a typical kit for determination, buffer, distilled water, or ultra-pure water according to needs so long as the component does not interfere with effects of the present invention.

The kit of such a form to practice the determination method according to the present invention may also serve as a kit to practice the diagnosis method according to the present invention.

In other words, the above-described kit to practice the determination method according to the present invention may serve as a kit to practice the diagnosis of the progressing stage to diabetic nephropathy or of a hepatic disease or rheumatoid arthritis.

The former kit to practice the diagnosis of the progressing stage of diabetic nephropathy determines heparan sulfate contained in urine specimens of healthy subjects and diabetics without nephropathy. By use of the kit, a progressing stage from diabetes to diabetic nephropathy may be diagnosed through determination of change in heparan sulfate in a diabetic.

Therefore, the kit to practice the diagnosis of the progressing stage of diabetic nephropathy basically contains elements identical to those of the above-described kit. However, the kit preferably contains an element especially required for the determination of heparan sulfate contained in urine as a specimen.

The latter kit diagnoses the hepatic disease or rheumatoid arthritis by characterizing the difference in a quantity and/or a quality between heparan sulfate contained in a blood specimen sampled from a healthy person and heparan sulfate contained in a blood specimen sampled from a patient suffering from hepatic disease or rheumatoid arthritis.

Therefore, the kit to practice the diagnosis of a hepatic disease or rheumatoid arthritis contains elements identical to those of the above-described kit. However, the kit preferably contains an element especially required for the detection of heparan sulfate contained in a blood specimen. Furthermore, in addition to these elements, the kit may contain an element for detection depending on a hepatic disease or rheumatoid arthritis.

More specifically, the kit to specifically detect a hepatic disease may contain an element such as the above-described liver disorder test, liver function test, or HBs antigen/antibody test. Also, the kit to specifically detect rheumatoid arthritis may contain an element such as IgG-RF test in blood.

These kits according to the present invention enable simple and accurate practice of the diagnosis method and facilitate the diagnosis of a progressing stage of diabetic nephropathy or diagnosis of a hepatic disease or rheumatoid arthritis. Thus, appropriate therapy may be attained based on information obtained from these diagnoses.

The present invention will next be described in more detail by way of examples, which should not be construed as limiting the invention thereto.

Analysis of Antigenic Determinant of Anti-heparan Sulfate Antibody 10E4

The antigenic determinant of anti-heparan sulfate antibody 10E4 was studied through investigation of changes in reactivity of anti-heparan sulfate antibody 10E4 associated with changes in the sulfate group of the heparan sulfate molecule.

Briefly, the following materials 1) through 4) were individually added onto plates to which anti-heparan sulfate antibody 10E4 had been attached:

1) bovine kidney heparan sulfate of different concentrations (Seikagaku Corp.; Lot No. S94Z02: HS(BK)), 2) a modified bovine kidney sulfate of 1) (CDSNAc-HS)—in which heparan sulfate had been completely desulfonated, 3) another modified bovine heparan sulfate (CDSNS-HS) which had been obtained by re-introducing sulfate groups to the N- positions of the CDSNAc-HS), and 4) still another modified bovine heparan sulfate (NDSNAc-HS) which had been obtained by completely removing the sulfate groups of the heparan sulfate of 1) at the N-positions only.

Simultaneously, biotin-labeled heparan sulfate was added so as to cause a competitive antigen-antibody reaction with the plate-attached anti-heparan sulfate antibody 10E4.

The heparan sulfate, respective modified heparan sulfate products, and biotin-labeled heparan sulfate, all of which had not reacted with anti-heparan sulfate antibody 10E4, were removed by washing. Subsequently, biotin was detected through use of peroxidase-labeled streptavidin. Enzymatic activity of the peroxidase was determined as described hereinafter, through use of hydrogen-peroxide-containing TMB solution as the color-developing substrate, and absorbance at 450 nm as an index (FIG. 1). In FIG. 1, the X-axis indicates the amount of heparan sulfate or respective modified heparan sulfates and the Y-axis indicates absorbance (O.D.).

From the results shown in FIG. 1, it is concluded that the reactivity of anti-heparan sulfate antibody 10E4 is affected by the presence or absence of the glucosamine residue with an N-sulfate group in heparan sulfate.

In other words, the antigenic determinant for anti-heparan sulfate antibody 10E4 contains at least the glucosamine residue with the N-sulfate group-containing structure in heparan sulfate.

Moreover, cross-reactivity of anti-heparan sulfate antibody 10E4 to hyaluronic acid was studied through investigation of same protocol of above mentioned using hyaluronic acid instead of heparan sulfate and it's derivative. From the result, it is shown that anti-heparan sulfate antibody exhibits no cross-reactivity to hyaluronic acid.

Preparation of a Calibration Curve (1) Preparation of Biotin-labeled Heparan Sulfate Heparan sulfate (Seikagaku Corp.) was dissolved in 0.1M 2-morpholinoethanesulfonic acid (MES) buffer (pH 5.5) to prepare a 10 mg/ml heparan sulfate solution (1 ml). To the thus-obtained heparan sulfate solution were added 25 µl of 20 mM biotin-LC-hydrazide (product of Pierce) in dimethylsulfoxide (DMSO). Subsequently, 12.5 µl of 100 mg/ml EDC (product of Pierce) in 0.1M MES buffer (pH 5.5) were added thereto. The mixture was stirred well and allowed to react for 16–24 hours at room temperature with stirring. After completion of reaction, the reaction product was subjected to dialysis (cutoff of the dialysis membrane: MW 3,500; dialysing buffer: PBS(−), etc.) by use of a microdialyzer (manufactured by Bio-Teck) until free biotin-LC-hydrazide was sufficiently removed. After dialysis, biotin-labeled heparan sulfate was prepared to have a concentration of 5 mg/ml and frozen for storage.

(2) Preparation of a Plate Coated with Anti-heparan Sulfate Antibody

Anti-heparan sulfate antibody 10E4 (Seikagaku Corp.) was diluted with phosphate-buffered saline (pH 7.2–7.5; divalent ions such as $Ca^{++}$ being not contained; hereinafter may be described as PBS(−)) to 20 μg/ml. A 50 μl aliquot of the resultant solution was added to each well of Nunc's immunoplate (trade name: MAXISOAP, product of Nunc.) and allowed to stand for 14–18 hours at 4° C., to thereby effect uniform coating of the wells. The plate was washed twice with PBS(−). Subsequently, in order to block portions of the wells that had not been covered by anti-heparan sulfate antibody 10E4, 3% bovine serum albumin (BSA) (sold by Seikagaku Corp.) in PBS(−) was added and the plate was left to stand for 2 hours at room temperature. Thereafter, the plate was washed three times with a washing buffer (PBS(−) containing 0.05% Tween 20) to thereby obtain the antibody-coated plate of interest; i.e., a plate coated with anti-heparan sulfate antibody 10E4.

(3) Preparation of a Calibration Curve

Subsequent to washing, PBS(−) supplemented with 0.05% Tween 20 and 1% BSA (hereinafter referred to as a reaction mixture) was added to each well of the anti-heparan sulfate antibody-coated plate prepared in (2) above in an amount of 100 μl. Subsequently, 10 μl of standard heparan sulfate solutions having different concentrations (derived from bovine kidneys; product of Seikagaku Corp.; various concentrations between 25 and 800 μg/ml) were added to each well. To each well were further added 100 μl of biotin-labeled heparan sulfate prepared in (1) above and diluted with the reaction mixture to have an optimum concentration, and the well was left to stand for 60 minutes at 37° C. for antigen-antibody reaction. (The solvent for preparing the standard heparan sulfate solutions was the reaction mixture.)

After completion of reaction, the wells were washed three times with the aforementioned washing buffer. Peroxidase-labeled streptavidin (HRP-labeled streptavidin: product of Vector) which had been diluted with the reaction mixture to a 1/1,000 concentration was added to the wells of the plate in an amount of 100 μl per well, and the plate was left to stand for 30 minutes at 37° C.

Figure 2:
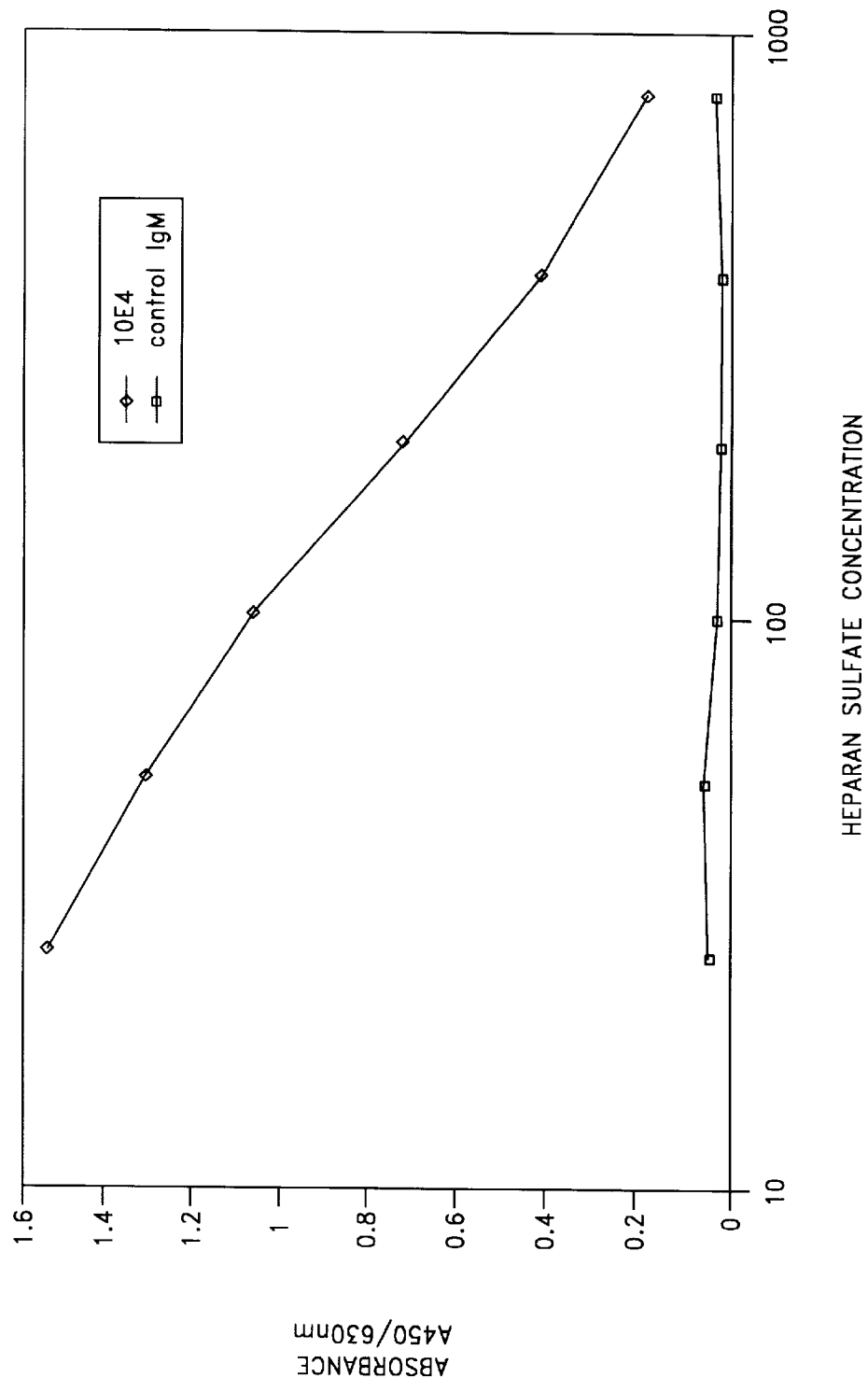
FIG. 2 shows the calibration curve prepared by use of standard heparan sulfate solution.

After completion of reaction, the plate was washed three times with the washing buffer, and to each well was added 100 μl of TMB solution (product of Moss) which served as a substrate for peroxidase. Reaction was allowed to proceed at 37° C. for 15 minutes, to thereby develop color. The reaction was stopped by the addition of 100 μl of 1N-HCl to the plate. Absorbance of the solution which had developed color due to decomposition of TMB was measured at the wavelength of 450 nm (reference wavelength: 630 nm) through use of a Wellreader (SK-601, sold by Seikagaku Corp.), to thereby create a calibration curve (FIG. 2).

In consideration of the wide diversity of heparan sulfate, the titer of heparan sulfate was expressed in terms of bovine kidney heparan sulfate equivalent (EU), based on the inventors' definition in which 1 μg of bovine kidney heparan sulfate (Seikagaku Corp., Lot No. S94Z02) corresponds to 1 EU.

Moreover, it was noted that, when the plate was coated with mouse IgM as a substitute for anti-heparan sulfate antibody, no reaction was observed. From this, it is concluded that the reaction was not nonspecific but specific to anti-heparan sulfate antibody (10E4) (FIG. 2: control).

Diagnosis by the Detection of Heparan Sulfate Contained in a Specimen (1) Diagnosis of the Progressing Stage of Diabetes Patients to Diabetic Nephropathy Urine specimens from healthy subjects (27 cases) and diabetes patients (68 cases) were used for quantitative determination of heparan sulfate present in the specimens.

Briefly, diabetes patients were divide into three groups of DM1, DM2, and DM3 based on urine albumin concentration (creatinine-corrected: ACR; mg/gCR). Each DM1 group patient had an ACR of lower than 12, and thus was on the same level as a healthy subject as far as ACR is concerned. The DM2 group patients, having ACR of equal to or higher than 12 and lower than 220, represent incipiental diabetic nephropathy, and the DM3 group patients, having ACR of equal to or higher than 220, represent diabetic nephropathy.

Figure 3:
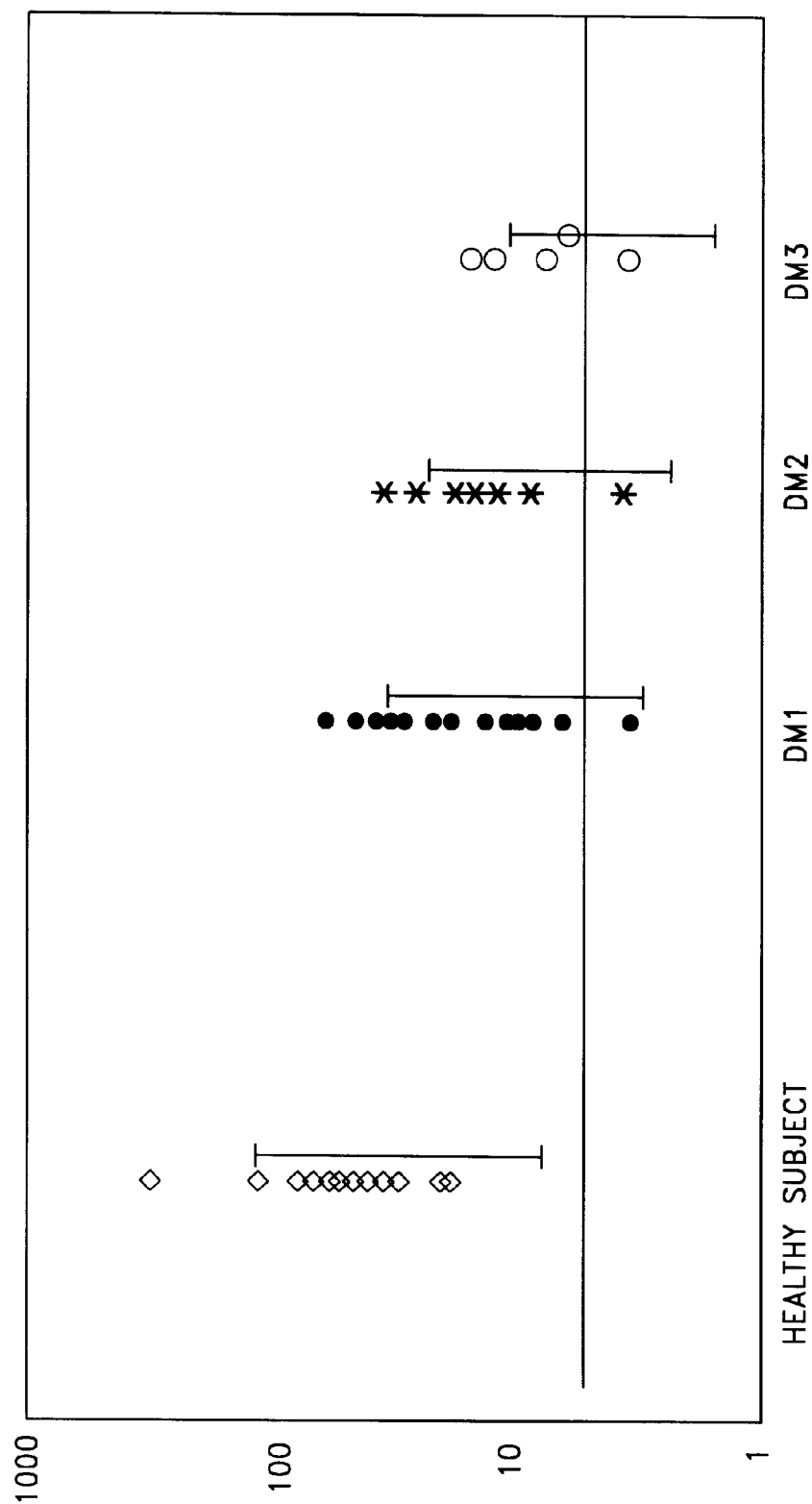
FIG. 3 shows comparison in levels of heparan sulfate contained in urine specimens between groups (DM1, DM2, DM3) indexed by albumin concentrations contained in urine specimens.

FIG. 3 shows heparan sulfate levels in urine specimens from the respective groups. Urinary heparan sulfate levels of diabetes patients (DM1) and those of healthy subjects were clearly distinguished. (The heparan sulfate level of a diabetes patient is clearly lower than that of a healthy subject.)

Figure 4:
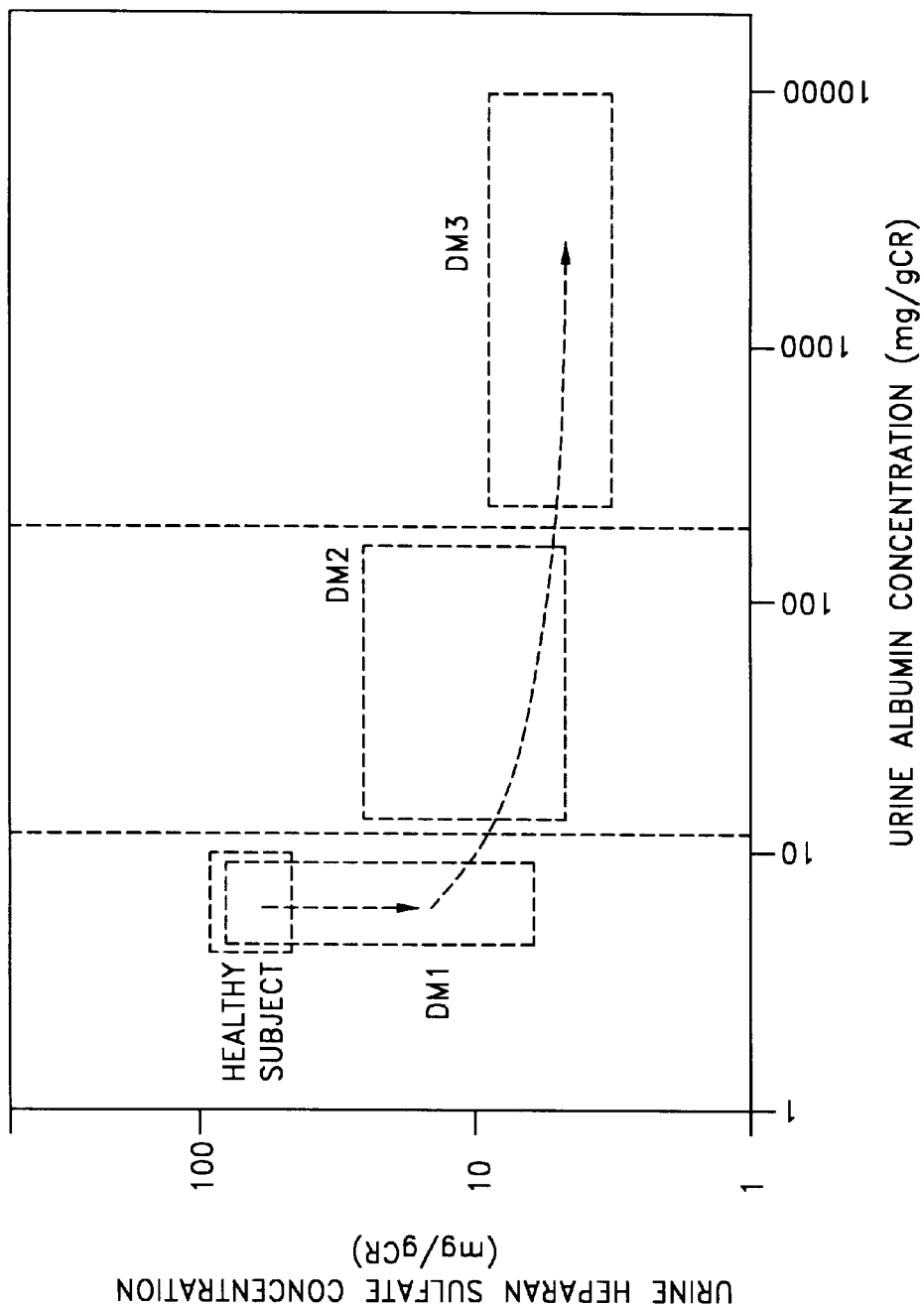
FIG. 4 shows comparison between albumin and heparan sulfate concentrations contained in urine specimens and distribution thereof.

Independently, urine specimens were collected from healthy subjects (83 cases), DM1 patients (40 cases), DM2 patients (41 cases), and DM3 patients (43 cases). Measurements of albumin concentration (creatinine-corrected: ACR; mg/gCR) and heparan sulfate concentration (creatinine-corrected; mg/gCR) in the urine specimens were plotted and their ranges of distribution were analyzed (FIG. 4). The healthy subjects and DM1 patients showed the same level of albumin concentration in urine specimens. In contrast, heparan sulfate concentrations in urine specimens from DM1 patients exhibited a broad distribution, ranging from the same level as healthy subjects to as low as about 1/10 the level of healthy subjects. It is considered that a tendency of the heparan sulfate concentration in urine specimens to decrease with the progress of symptoms of diabetic nephropathy is already observed in the DM1 stage. In addition, DM1 patients exhibiting low heparan sulfate concentrations in urine specimens are considered to run a high risk of progress to incipiental diabetic nephropathy (DM2).

Figure 5:
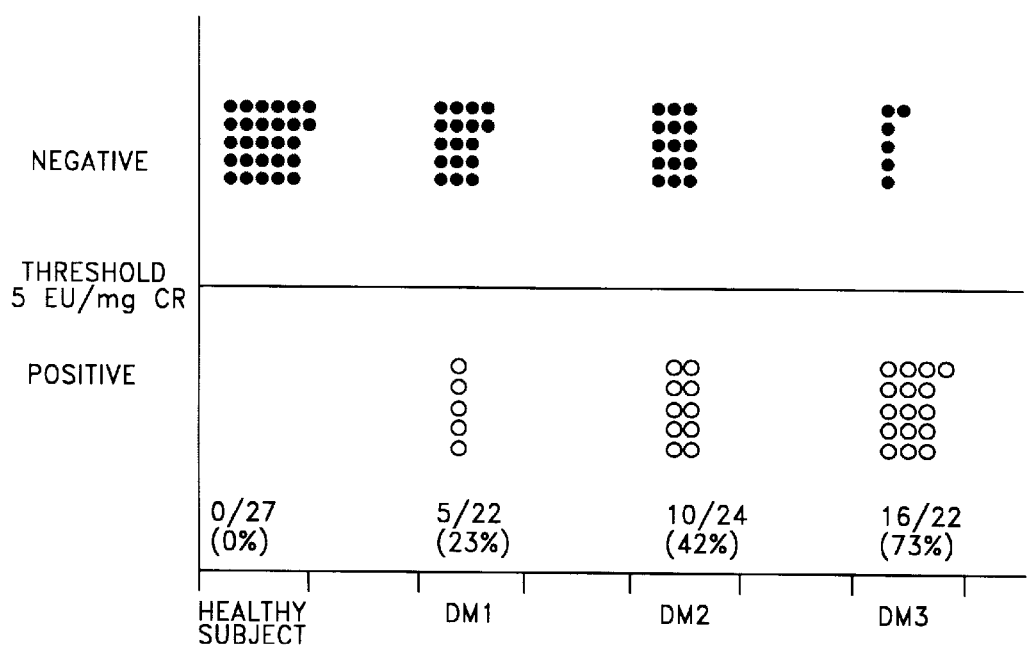
FIG. 5 shows correlation between the conditions of diabetic nephropathy and the level of heparan sulfate lower or not lower than the threshold level of 5 EU/mg CR.

Thus, assuming that the value 5 EU/mg CR was a threshold, the test subjects were classified into "negative" for values equal to or higher than the threshold, and "positive" for values lower than the threshold. As a result, it was found that as diabetic nephropathy progresses, the number of "positive" subjects increases (FIG. 5). This suggests that setting of a 5 EU/mg CR threshold is preferable in the practice of the detection method of the present invention on the basis of the heparan sulfate amount quantitatively determined in urine specimens according to the quantitative determination method of the present invention.

Figure 6:
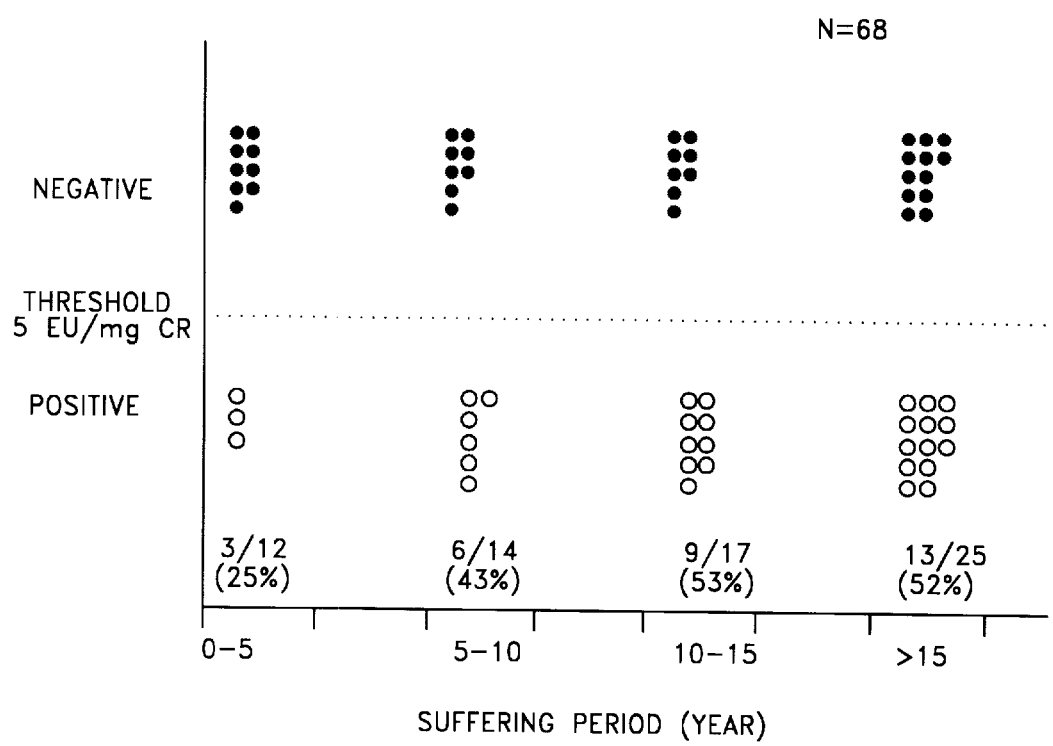
FIG. 6 shows correlation between the duration of diabetes and the level of heparan sulfate lower or not lower than the threshold level of 5 EU/mg CR.

Moreover, when the data were classified in terms of the suffering period of diabetes related to the onset of diabetic nephropathy, the number of "positive" cases were found to increase in association with the duration of diabetes (FIG. 6).

In view of the fact that after 5–10 years of suffering from diabetes increased numbers of patients tend to be diagnosed as incipiental diabetic nephropathy and after about 15 years of suffering from diabetes increased numbers of patients tend to be diagnosed as diabetic nephropathy, the results in FIG. 6 support the utility of the quantitative determination method and the diagnostic method of the present invention, as the results in FIG. 6 show that the diagnostic method of the present invention established on the technical basis of the quantitative determination method of the present invention enables diagnostic of the progressing stage of the condition to diabetic nephropathy.

(2) Diagnosis of Hepatic Diseases or Rheumatoid Arthritis

The levels of heparan sulfate in serums of 141 healthy subjects, 42 patients suffering from osteoarthritis, 54 patients suffering from hepatic disease, and 54 patients suffering from rheumatoid arthritis were quantitatively determined according to the method described above (FIG. 7).

The results show that the levels of heparan sulfate in serums of patients suffering from hepatic diseases or rheumatoid arthritis were significantly lower than those of healthy subjects.

Figure 7:
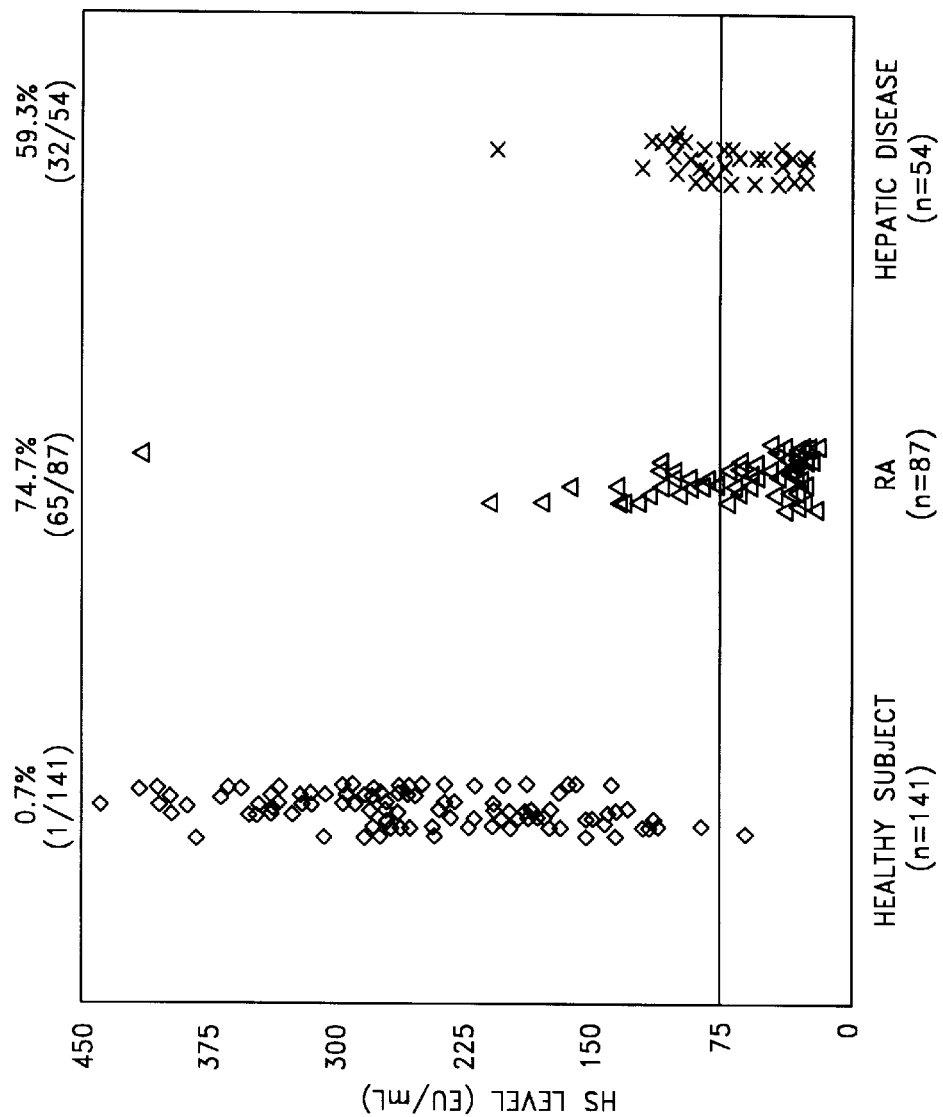
FIG. 7 shows comparison in levels of heparan sulfate contained in serums between groups as well as the positive percentages of hepatic diseases or rheumatoid arthritis as diagnosed when 75 EU/ml is applied as the threshold level.

A tentative threshold level of heparan sulfate was set at 75 EU/ml. Levels not lower than 75 EU/ml were defined as negative, and levels lower than 75 EU/ml were defined as positive. FIG. 7 shows the positive rates in patients suffering from hepatic diseases and rheumatoid arthritis.

The results suggest that setting a threshold level of heparan sulfate so as to diagnose diseases is favorable for detecting diseases easily based on serum heparan sulfate quantitatively determined according to the present invention.

In addition, in order to prove the usefulness of the diagnostic method of the present invention, there were compared and studied the positive rate in each specimen determined by the method for diagnosing hepatic diseases and rheumatoid arthritis of the present invention; that determined by the IgG-RF quantitative determination method by use of a commercially available IgG-RF measuring kit (brand name: Eitest IgGRF; product of Eisai Co., Ltd.); and that determined by the hyaluronic acid quantitative determination method by use of a hyaluronic acid measuring kit (for detecting hepatic diseases; brand name: Hyaluronic Acid Plate "Chugai"; product of Chugai Pharmaceutical Co., Ltd.).

In the diagnostic method of the present invention, a threshold level of heparan sulfate was set at 75 EU/ml, as was set above. The determined levels lower than 75 EU/ml were defined as positive. In diagnosis by use of the IgG-RF measuring kit, a test using Index 2 was performed for serums of healthy subjects and those of patients suffering from rheumatoid arthritis according to the method described in the manual. In diagnosis by use of the hyaluronic acid measuring kit, levels higher than 130 ng/ml as determined hyaluronic acid levels in serums of healthy subjects and serums of patients suffering from hepatic diseases, according to the method described in the manual, were defined as positive.

The positive rates among healthy subjects, i.e. false positive, were compared. The results show that the diagnostic method of the present invention yields a considerably low false positive percentage (Table 1).

TABLE 1

| Diagnostic Method | IgG-RF Diagnostic Method | Hyaluronic Acid Diagnostic Method | Diagnostic Method of the Present Invention |
| --- | --- | --- | --- |
| False Positive Percentage | 2.7% | 8.7% | 0.7% |

The positive percentages in serums of patients suffering from rheumatoid arthritis were calculated based on the levels as determined by the IgG-RF quantitative determination method and the quantitative determination method of the present invention. Diagnosis of rheumatoid arthritis by the quantitative determination method of the present invention was shown to be about twice as precise as that by the IgG-RF quantitative determination method (Table 2).

TABLE 2

| Diagnostic Method | IgG-RF Diagnostic Method | Diagnostic Method of the Present Invention |
| --- | --- | --- |
| Positive Percentage | 38.7% | 74.7% |

The positive percentages in patients suffering from hepatic diseases were calculated according to the hyaluronic acid diagnostic method and according to the diagnostic method of the present invention. Diagnosis of hepatic diseases by the diagnostic method of the present invention was shown to be highly precise, and more precise than that by the hyaluronic acid diagnostic method (Table 3).

TABLE 3

| Measuring Method | Hyaluronic Acid Measuring Method | The Present Invention |
| --- | --- | --- |
| Positive Percentage | 56.7% | 59.3% |

According to these results, it is concluded that the diagnostic method of the present invention permits more highly precise diagnosis of hepatic diseases and rheumatoid arthritis than those achieved by the other methods, thus lowering the false positive percentage.

Kits of the Present Invention

The constitution and use of the kits of the present invention will now be described.

The kits of the present invention—both types for diagnosing a progressing stage of diabetic nephropathy and for diagnosing hepatic diseases and rheumatoid arthritis—comprise the following components 1–8.

1. an immunoplate to which anti-heparan sulfate antibody 10E4 is coated (pre-blocked with a blocking agent): 1 piece
2. standard heparan sulfate solutions (25, 50, 100, 200, 400, 800 EU/ml, 0.1 ml each): 1 vial each
3. biotin-labeled heparan sulfate solution (optimum concentration, 15 ml): 1 vial
4. peroxidase-labeled streptavidin solution (1 $\mu$g/ml, 15 ml): 1 vial
5. tetramethylbenzidine solution (1.25 mM TMB, 2.21 mM hydrogen peroxide, 1% DMSO, 0.08 M acetic acid buffer, pH 4.9, 15 ml): 1 vial
6. reaction buffer (1% BSA, PBS(-) containing 0.05% Tween 20, 40 ml): 1 vial
7. washing buffer (PBS(-) containing 0.05% Tween 20, 500 ml): 1 vial
8. reaction stop solution (1N HCl, 15 ml): 1 vial In use of the kits of the present invention, each well on the immunoplate to which anti-heparan sulfate antibody 10E4 was coated was pre-washed with the washing liquid, and the reaction buffer (100 $\mu$l each) was poured into each well.

In use of the kit for diagnosing a progressing stage of diabetic nephropathy, to each well was added to the kit the standard heparan sulfate solution of each concentration or a urine specimen of a diabetic (10 $\mu$l each), and the biotin-labeled heparan sulfate solution (100 $\mu$l each) was further added to each well. The plate was allowed to stand for 60 minutes at 37° C.

In use of the kit for diagnosing hepatic diseases and rheumatoid arthritis, to each well was added the standard heparan sulfate solution of each concentration or a serum specimen of a patient suffering from a hepatic disease or rheumatoid arthritis (10 µl each), and the biotin-labeled heparan sulfate solution (100 µl each) was added to each well. The plate was allowed to stand for 60 minutes at 37° C.

Subsequently, in both of the kits, each well was washed with the washing buffer three times, and then the peroxidase-labeled streptavidin solution (100 µl each) was added to each well. The plate was allowed to stand for 30 minutes at 37° C.

Subsequently, each well was washed three times with the washing buffer, and then the tetramethylbenzidine solution (100 µl each) was added to each well. The mixture was allowed to stand for 15 minutes at 37° C. and develop color.

After the color development, reaction stop solution (100 µl) was added to each well to terminate the reaction. The absorbance at 450 nm, which is the optimal wavelength of the colored reaction product produced by the reaction between TMB and $H_2O_2$ in the presence of peroxidase, was determined by use of a Wellreader (SK601, sold by Seikagaku Corp.).

As described above, the present invention provides a quantitative determination method for accurately determining heparan sulfate contained in specimens. The present invention also provides a diagnostic method for judging the condition of diabetics and their progressing stages in the course of progress to diabetic nephropathy by use of the quantitative determination method for determining heparan sulfate contained in urine specimens. The present invention further provides a kit to practice the diagnostic method. In addition, the present invention provides a diagnostic method for diagnosing hepatic diseases and rheumatoid arthritis by using the quantitative determination method for determining heparan sulfate contained in blood specimens. The present invention further provides a diagnostic kit to practice the method.

What is claimed is:

1. A method for quantitatively determining heparan sulfate contained in a specimen solution, which comprises the steps of:
    (a) contacting the specimen solution with an anti-heparan sulfate antibody immobilized on a solid phase, wherein said anti-heparan sulfate antibody exhibits no cross-reactivity with hyaluronic acid;
    (b) subjecting heparan sulfate contained in the specimen solution to antigen-antibody reaction with the anti-heparan sulfate antibody on the solid phase to form an antigen-antibody complex;
    (c) labeling the antigen-antibody complex with a labeling substance;
    (d) removing residues other than the labeled antigen-antibody complex from the solid phase;
    (e) detecting the labeling substance as an index of a quantity of the labeled antigen-antibody complex on the solid phase; and
    (f) calculating the quantity of heparan sulfate contained in the specimen solution based on a calibration curve obtained using a standard solution with the labeling substance.

2. The method according to claim 1, wherein said antigen-antibody reaction is a competitive antigen-antibody reaction between labeled heparan sulfate and heparan sulfate contained in the specimen solution with respect to the anti-heparan sulfate antibody attached to the solid phase.

3. The method according to claim 2, wherein the method further comprises the step of detecting said labeled heparan sulfate bound to the anti-heparan sulfate antibody on the solid phase, to thereby quantitatively determine the heparan sulfate contained in the specimen.

4. The method according to claim 2, wherein said labeling substance is selected from the group consisting of a counterpart of specific binding pair, a fluorescent substance, an enzyme, and a radioactive isotope.

5. The method according to claim 4, wherein said counterpart of specific binding pair is biotin.

6. A method for quantitatively determining heparan sulfate contained in a specimen solution, which comprises the steps of:
    a) contacting a specimen solution with biotin-labeled heparan sulfate on a microplate on which an anti-heparan sulfate antibody exhibiting specificity for at least an antigenic determinant of glucosamine residue with an N-sulfate group in heparan sulfate is attached, and causing a competitive antigen-antibody reaction between said biotin-labeled heparan sulfate and said heparan sulfate with respect to said anti-heparan sulfate antibody, said anti-heparan sulfate antibody exhibiting no cross reactivity with hyaluronic acid;
    b) binding avidin labeled with peroxidase to said biotin-labeled heparan sulfate attached to said anti-heparan sulfate antibody on the microplate; and
    c) measuring activity of said peroxidase.

7. The method according to claim 1, wherein said anti-heparan sulfate antibody exhibits specificity for at least an antigenic determinant of glucosamine residue with an N-sulfate group in heparan sulfate.

8. The method according to claim 7, wherein said anti-heparan sulfate antibody is anti-heparan sulfate monoclonal antibody 10E4.

9. A method for quantitatively determining heparan sulfate contained in a specimen solution, which comprises the steps of:
    (a) contacting the specimen solution with a solid phase on which heparan sulfate is immobilized;
    (b) adding an anti-heparan sulfate antibody onto the solid phase, wherein said anti-heparan sulfate antibody exhibits no cross-reactivity with hyaluronic acid;
    (c) subjecting heparan sulfate contained in the specimen solution and the immobilized heparan sulfate to antigen-antibody reaction with the anti-heparan sulfate antibody to form an antigen-antibody complex;
    (d) labeling the antigen-antibody complex with a labeling substance;
    (e) removing from the solid phase, residues other than the labeled antigen-antibody complex immobilized on the solid phase;
    (f) detecting the labeling substance as an index of a quantity of the labeled antigen-antibody complex on the solid phase; and
    (g) calculating the quantity of heparan sulfate contained in the specimen solution based on a calibration curve obtained using a standard solution with the labeling substance.

10. A method for quantitatively determining heparan sulfate contained in a specimen solution, which comprises the steps of:
    (a) contacting the specimen solution with a microparticulate solid phase on which heparan sulfate is immobilized;
    (b) adding an anti-heparan sulfate antibody into the specimen solution, wherein said anti-heparan sulfate antibody exhibits no cross-reactivity with hyaluronic acid;

(c) subjecting heparan sulfate contained in the specimen solution and the immobilized heparan sulfate to competitive antigen-antibody reaction with the anti-heparan sulfate antibody to form aggregates of the microparticulates via antigen-antibody complexes;

(d) removing residues other than the aggregates from the solid phase;

(e) detecting the degree of aggregation of the microparticulates as an index of a quantity of the antigen-antibody complex formed on the microparticulates; and (f) calculating the quantity of heparan sulfate contained in the specimen solution based on a calibration curve obtained using a standard solution containing a known quantity of heparan sulfate in place of the specimen solution.

11. The method according to claim 9, wherein said antigen-antibody reaction is a competitive antigen-antibody reaction between heparan sulfate attached to the solid phase and heparan sulfate contained in the specimen solution with respect to the anti-heparan sulfate antibody.

12. The method according to claim 11, wherein the method further comprises the step of detecting an anti-heparan sulfate antibody bound to the heparan sulfate on the solid phase or in the specimen, to thereby quantitatively determine the heparan sulfate contained in the specimen.

13. The method according to claim 12, wherein said anti-heparan sulfate antibody exhibits specificity for at least an antigenic determinant of glucosamine residue with an N-sulfate group in heparan sulfate.

14. The method according to claim 13, wherein said anti-heparan sulfate antibody is anti-heparan sulfate monoclonal antibody 10E4.

15. The method according to claim 10, wherein said anti-heparan sulfate antibody exhibits specificity for at least an antigenic determinant of glucosamine residue with an N-sulfate group in heparan sulfate.

16. The method according to claim 15, wherein said anti-heparan sulfate antibody is anti-heparan sulfate monoclonal antibody 10E4.

17. A method for diagnosing a progressing stage of incipiental diabetic nephropathy or diabetic nephropathy, comprising the steps of: subjecting heparan sulfate contained in a urine specimen to antigen-antibody reaction with an anti-heparan sulfate antibody; and quantitatively detecting the presence of heparan sulfate in the urine specimen reacted with the anti-heparan sulfate antibody.

18. The method according to claim 17, wherein said anti-heparan sulfate antibody is anti-heparan sulfate monoclonal antibody 10E4.

19. The method according to claim 1, wherein the specimen solution is a body fluid specimen.

20. The method according to claim 1, wherein the specimen solution is a urine specimen.

* * * * *